US006274766B1

(12) United States Patent
Jackman et al.

(10) Patent No.: US 6,274,766 B1
(45) Date of Patent: Aug. 14, 2001

(54) PROCESS FOR PURIFYING α-KETO ACIDS

(75) Inventors: Dennis E. Jackman, Prairie Village, KS (US); Cathy L. Howerton, Independence, MO (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/315,073

(22) Filed: May 19, 1999

(51) Int. Cl.[7] ............................ C07C 59/74; C07C 59/76; C07C 59/147
(52) U.S. Cl. ............................................. 562/577; 562/512
(58) Field of Search .................................... 562/580, 577, 562/512

(56) References Cited

U.S. PATENT DOCUMENTS

| 2,092,494 | * | 9/1937 | Bass et al. . | |
| 3,524,877 | * | 8/1970 | Haage et al. . | |
| 4,013,680 | * | 3/1977 | Johnson et al. . | |
| 4,175,188 | | 11/1979 | Klenk et al. | 544/182 |
| 4,204,044 | * | 5/1980 | Suhara et al. . | |
| 4,614,822 | | 9/1986 | Jackman et al. | 544/182 |

* cited by examiner

*Primary Examiner*—Paul J. Killos
*Assistant Examiner*—Mahreen Chaudhry
(74) *Attorney, Agent, or Firm*—Joseph C. Gil

(57) ABSTRACT

The present invention relates to an improved process for purifying α-keto acids. In particular, the present invention pertains to the isolation of pivalic acid and other organic impurities from α-keto acids. The process of the invention generally includes (i) the partial acidification of an aqueous solution of a sodium salt of the α-keto acid (a"keto salt"), (ii) a first solvent extraction of the keto salt solution to remove organic impurities, (iii) further acidification of the keto salt solution, (iv) a second solvent extraction to remove the α-keto acid, and (v) isolation of the α-keto acid from the solvent. In a preferred embodiment, the present invention relates to the preparation of trimethylpyruvic acid (TMPA) of enhanced purity.

9 Claims, No Drawings

PROCESS FOR PURIFYING α-KETO ACIDS

FIELD OF THE INVENTION

The present invention relates to an improved process for purifying α-keto acids. In particular, the present invention pertains to the isolation of pivalic acid and other organic impurities from α-keto acids. In a preferred embodiment, the present invention relates to the preparation of trimethylpyruvic acid (TMPA) of enhanced purity.

BACKGROUND OF THE INVENTION

It is known that α-keto acids and salts thereof are useful as starting materials in the production of herbicides. In particular, ar aqueous solution of the sodium salt of TMPA is used in the synthesis of the herbicide Sencor. In the prior art, various processes for producing α-keto acids and salts thereof have been proposed. These processes include (1) reacting sodium cyanide and acetyl chloride to form acetyl cyanide and then hydrolyzing the cyanide; (2) dry-distilling tartaric acid in the presence of potassium hydrogensulfate; (3) fermenting lactic acid; (4) oxidizing lactic esters with potassium permanganate; and (5) oxidizing propylene glycol.

In U.S. Pat. No. 4,175,188, a process is described for producing TMPA from trimethylpyruvic acid N-t-butylamide. The process includes the acid hydrolysis of trimethylpyruvic acid N-t-butylamide by heating under reflux in hydrochloric acid, and then extracting with dilute sodium hydroxide, hydrochloric acid and ethyl acetate. The yield of the desired product is only 75% of theory.

In U.S. Pat. No. 4,614,822, a process is described for preparing TMPA by oxidation of the corresponding α-hydroxy acid.

The above-identified processes have various disadvantages which include the following: (i) the yield of the desired product is low, and (ii) the formation of considerable amounts of by-products makes it difficult to separate and purify the desired product.

SUMMARY OF THE INVENTION

It is an object of the present invention to provide a process for preparing α-keto acids of enhanced purity. The object of the invention is realized by (i) adding to an aqueous solution of a sodium salt of the α-keto acid (a "keto salt") a mineral acid in an amount such that the pH of the acidified solution is from about 3.0 to about 4.0; (ii) adding a solvent to the acidified solution and allowing the resultant mixture to separate into a first organic phase and a first aqueous phase; (iii) removing the first organic phase from the first aqueous phase, wherein the first organic phase includes the solvent and organic impurities, and wherein the first aqueous phase includes water and the sodium salt of the α-keto acid ("keto salt"); (iv) adding a mineral acid to the first aqueous phase in an amount such that the pH of the acidified first aqueous phase is less than 1; (v) adding a solvent to the acidified first aqueous phase and allowing the resultant mixture to separate into a second organic phase and a second aqueous phase; (vi) removing the second organic phase from the second aqueous phase, wherein the second organic phase includes the solvent and α-keto acid, and the second aqueous phase includes water; and (vii) recovering the α-keto acid of enhanced purity from the second organic phase.

DETAILED DESCRIPTION OF THE INVENTION

The process of the present invention relates to preparing α-keto acids of enhanced purity. The process generally includes the partial acidification of an aqueous solution of a sodium salt of the α-keto acid (a "keto salt"), a first solvent extraction of the keto salt solution to remove organic impurities, further acidification of the keto salt solution, a second solvent extraction to remove the α-keto acid, and isolation of the α-keto acid from the solvent.

In the present invention, a mineral acid is added to an aqueous solution of a sodium salt of the α-keto acid (a "keto salt"). Suitable mineral acids include hydrochloric acid, sulfuric acid, and phosphoric acid. In a preferred embodiment, the mineral acid is hydrochloric acid. The mineral acid is added in an amount such that the pH of the acidified solution is from about 3.0 to about 4.0, and preferably from about 3.3 to about 3.7. The mineral acid used in the reaction mixture is preferably an aqueous solution containing from about 30% by weight to about 100% by weight of mineral acid, and preferably from about 37% to about 85% by weight of mineral acid. The precise amount of mineral acid used in the reaction depends on the particular mineral acid selected. Further, in a preferred embodiment, the keto salt solution is an aqueous trimethylpyruvic acid (TMPA) salt solution, and the purified α-keto acid is TMPA.

A solvent is then added to the acidified keto salt solution. Preferably, the solvent is an organic solvent. Such suitable organic solvents are known in the art and include any water insoluble ketones, esters, ethers, alcohols, hydrocarbons, and chlorinated hydrocarbons. In a preferred embodiment, the solvent is either ethyl acetate or methyl-isobutyl ketone (MIBK). The ratio of the keto salt solution to solvent by volume is from about 1:1 to about 10:1, and preferably from about 3:1 to about 5:1. Addition of the solvent to the keto salt solution results in a mixture that is separated into a first organic phase and a first aqueous phase. The first organic phase contains the solvent and organic impurities. The first aqueous phase includes water and keto salt. The first organic phase, containing the impurities, is removed from the first aqueous phase.

A mineral acid is then added to the first aqueous phase. The mineral acid for this second acidification step may be selected from the same group as that previously indicated for the first acidification step of the invention. In a preferred embodiment, the mineral acid is hydrochloric acid. The mineral acid is added in an amount such that the pH of the acidified solution is less than 1, and preferably from about 0.4 to about 0.8. The mineral acid has a concentration of from about 30% to about 100% by weight, and preferably from about 37% to about 85% by weight. The precise amount of mineral acid used in the reaction will depend on the particular mineral acid selected.

A solvent is then added to the acidified first aqueous phase. The solvent may be selected from the same group as that indicated in the previous solvent extraction step. In a preferred embodiment, the solvent is MIBK. The ratio of keto salt solution to solvent by volume is from about 1:1 to about 10:1, and preferably from about 3:1 to about 5:1. Addition of the solvent results in a mixture that is separated into a second organic phase and a second aqueous phase. The second organic phase contains the solvent and α-keto acid. The second aqueous phase includes water and inorganic salts. The second organic phase is removed from the second aqueous phase.

The α-keto acid of enhanced purity is then isolated from the solvent in the second organic phase. In a preferred embodiment, isolation of the desired product is accomplished by distillation of the solvent from the second organic phase.

The process of the present invention may be carried out as either a batch process or a continuous process. Further, the solvent may be recovered from the first and second organic phases, and recycled for subsequent use in the process of the present invention.

The following examples illustrate preferred embodiments of the present invention and are not limiting of the specification and claims in any way.

EXAMPLES

Example 1

Isolation of TMPA in a Batch Process

About 3,057 grams of an aqueous TMPA salt solution were charged to a vessel. The TMPA salt solution was stirred and then about 68.4 grams of concentrated hydrochloric acid (HCl) were added. The resulting acidified solution had a pH of about 3.3. About 500 ml of MIBK was added to the acidified solution. This mixture was then stirred and allowed to settle. After about one minute, an organic layer and an aqueous layer were formed. The organic layer was removed from the aqueous layer. The aqueous layer was then divided into two portions.

a.) The first portion of the aqueous layer contained about 1552.5 grams of an acidified TMPA salt solution having a pH of 3.3. About 67.7 grams of concentrated HCl was added to the TMPA salt solution, resulting in an acidified mixture having a pH of about 0.7. About 310 grams of MIBK were then added to this acidified mixture. The mixture was stirred and allowed to settle. After about two minutes, an organic layer and an aqueous layer were formed. The organic layer was removed from the aqueous layer. The TMPA was isolated from the organic: layer by distillation of the MIBK at about 45° C. The net yield of the TMPA recovered in the organic layer was from about 90% to about 93%. The recovery of TMPA was increased to about 98% when a second MIBK extraction of the aqueous layer was performed.

b.) The second portion of the aqueous layer contained about 1552.5 grams of an acidified TMPA salt solution having a pH of 3.3. About 68.9 grams of concentrated HCl was added to the TMPA salt solution, resulting in an acidified mixture having a pH of about 0.7. The mixture was stirred and allowed to settle. After about eight minutes, an organic layer and an aqueous layer were formed. The organic layer was removed from the aqueous layer. The net yield of the TMPA recovered in the organic layer was about 61%. The TMPA in the aqueous layer may be recovered by extraction with MIBK.

Example 2

Isolation of TMPA in a Continuous Process

An aqueous TMPA salt solution and concentrated hydrochloric acid (HCl) were continuously pumped into a first vessel B1. The TMPA salt solution had a pH of from about 7 to about 11 and a purity of from about 7% to about 8%. The molar ratio of HCl to TMPA salt solution was such that the resulting mixture had a constant pH of from about 3 to about 4. This acidified TMPA salt solution was stirred and allowed to overflow into a second vessel B2, where it was continuously mixed with methyl isobutyl ketone (MIBK). The ratio of acidified TMPA salt solution to MIBK was maintained at about 5:1. The mixture from B2 then overflowed into a first separator S1, where the organic layer containing MIBK and impurities was removed from the aqueous layer containing water and TMPA salt. The aqueous layer flowed into a third vessel B3. In B3, HCl was continuously added to the mixture in such amount as to achieve a pH of approximately 0.7. At this point, the TMPA salt was completely converted to TMPA. The acidified B3 mixture then flowed into a fourth reactor B4, where a second solvent addition step took place. In B4, MIBK was continuously added in an amount sufficient to maintain the ratio of acidified TMPA solution to solvent of 5:1. The mixture in B4 then overflowed into a second separator S2, where the organic layer containing MIBK and TMPA was removed from the aqueous layer containing water. The desired TMPA product contained in the organic layer was isolated from the MIBK by distillation of the MIBK. The distillation was carried out at a reduced pressure so that the temperature did not exceed about 80° C. (TMPA can decompose at higher temperatures). A solvent extraction of the aqueous layer from separator S2 resulted in the complete recovery of TMPA. The MIBK was recovered from both the first and second organic layers by (i) distillation or (ii) removal of the acids by extraction with diluted sodium hydroxide.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing trimethylpyruvic acid of enhanced purity, comprising the steps of:
   a. adding a mineral acid to an aqueous solution of a sodium salt of the trimethylpyruvic acid, in an amount such that the pH of the acidified solution is from about 3.0 to about 4.0;
   b. adding an organic solvent to the acidified solution and allowing the resultant mixture to separate into a first organic phase and a first aqueous phase;
   c. removing the first organic phase from the first aqueous phase, wherein the first organic phase includes the solvent and organic impurities, and the first aqueous phase includes water and the sodium salt of the trimethylpyruvic acid;
   d. adding a mineral acid to the first aqueous phase in an amount such that the pH of the acidified first aqueous phase is less than 1;
   e. adding an organic solvent to the acidified first aqueous phase and allowing the resultant mixture to separate into a second organic phase and a second aqueous phase;
   f. removing the second organic phase from the second aqueous phase, wherein the second organic phase includes the solvent and the trimethylpyruvic acid, and the second aqueous phase includes water and inorganic salts; and
   g. recovering the trimethylpyruvic acid of enhanced purity from the second organic phase.

2. The process of claim 1 wherein the mineral acid is selected from the group consisting of hydrochloric acid, phosphoric acid and sulfuric acid.

3. The process of claim 1 wherein in step a) the pH of the acidified solution is from about 3.3 to about 3.5.

4. The process of claim 1 wherein the organic solvent is selected from the group consisting of water insoluble ketones, esters, ethers, alcohols, hydrocarbons and chlorinated hydrocarbons.

5. The process of claim 4 wherein the organic solvent is selected from the group consisting of ethyl acetate and methyl-isobutyl ketone.

6. The process of claim 1 wherein in step d) the pH of the acidified first aqueous phase is from about 0.4 to about 0.8.

7. The process of claim 1 wherein in step g) wherein the trimethylpyruvic acid is isolated via distillation of the solvent.

8. The process of claim 1 wherein the process is carried out continuously.

9. The process of claim 1 wherein said solvent is recovered from the first and the second organic phases and recycled for use in steps b) and e).

* * * * *